United States Patent [19]

Mulder

[11] Patent Number: Plant 6,770

[45] Date of Patent: May 2, 1989

[54] DAHLIA PLANT NAMED SIMON

[75] Inventor: Alle D. Mulder, Enkhuizen, Netherlands

[73] Assignee: Royal Sluis B.V., Enkhuizen, Netherlands

[21] Appl. No.: 131,373

[22] Filed: Dec. 10, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct Dahlia plant named Simon, having orange flower color, double flower form, dense foliage, compact flower bouquet carried above the foliage, compact growth habit, and an adaptability to pot plant or natural outdoor cultures.

1 Drawing Sheet

The present invention relates to a new and distinct cultivar of Dahlia plant known by the cultivar name Simon, and botanically known as *Dahlia cav.*

Simon was originated from a hybridization made by me in a controlled breeding program in 1983 in Enkhuizen, The Netherlands. The female parent was a Dahlia cultivar unknown at this time. The male parent of Simon was a selected plant of the seed varieties commercially well known under the name Figaro. Simon was discovered and selected by applicant as one flowering plant within the progeny of the stated parentage in a controlled environment in Enkhuizen, The Netherlands.

The first act of asexual reproduction of Simon was accomplished when tuberous divisions were taken by me from the new cultivar in Enkhuizen, The Netherlands. Subsequent horticultural examination of selected units has demonstrated that the combination of characteristics as herein disclosed for Simon are firmly fixed and are retained through successive generations of asexual reproduction.

Simon has not been observed under all possible environmental conditions. The phenotype may vary significantly with variations in environment such as temperature, light intensity, and day length. The following observations, measurements and comparisons describe plants grown in Enkhuizen, The Netherlands under greenhouse and outdoor conditions which approximate those generally used in commercial practice.

The following traits have been repeatedly observed and are determined to be basic characteristics of Simon, which in combination distinguish this Dahlia as a new and distinct cultivar:

(1) Attractive orange ray florets.

(2) Double flower form.

(3) Dense relatively dark green foliage, which provides a pleasant contrast with the flower color.

(4) The flowers are carried above the foliage in a compact bouquet.

(5) Compact growth habit.

(6) Adaptable to pot plant culture as well as natural outdoor growth.

Relevant cultivars for comparison purposes are varieties of Rigoletto, also a well known commercial Dahlia series obtained from seed, and plants of Figaro. In comparison to Rigoletto, Simon is more compact, has a double flower form, and white ray florets. Simon is distinguished from Figaro by its more compact habit, its earlier flowering, and its orange ray floret color.

The accompanying color photographic drawing shows typical inflorescence and foliage characteristics of Simon, with colors being as nearly true as possible with illustrations of this type. The photograph is a perspective view of several potted plants of Simon.

In the following description color references are made to The Royal Horticultural Society Colour Chart. The color values were determined at Enkhuizen, The Netherlands, and the characteristics noted below are based on plants grown at the same location.

Classification:

*Botanical.*—*Dahlia cav.* cv Simon (Group IV, peony flowered, classification of International Dahlia Register, 1969).

*Commercial.*—Dahlia.

Parentage:

*Female parent.*—Unknown at this time.

*Male parent.*—A plant of the Figaro series.

Plant:

*Form.*—Generally round.

*Size.*—20–22 cm in height (from top of pot).

*Growth habit.*—Compact.

*Foliage.*—Size: Small (according to Group classification noted above); 8–9 cm long and 4 cm wide. Quantity: Abundant, dense.

*Color.*—Dark green.

*Shape.*—Narrow, generally ovate, edges serrated.

*Texture.*—Relatively dull.

Flowers:

*Form.*—Double.

*Shape.*—Overall inflorescence is generally flat but also slightly curled and revolute, with petals having blunt or slightly rounded tips.

*Size.*—Individual ray florets are relatively small, being approximately 3–4 cm long and 1–1.5 cm wide; overall inflorescence approximately 8 cm in diameter.

*Borne.*—On pedicals which are approximately 6–7 cm in length; top of the pedicel oriented at approximately 90° to the vertical axis of the plant; flowers carried compactly above the foliage.

*Quantity.*—Floriferous.

*Stems.*—Color of both new stem and flowering stem is light green with anthocyanin coloration.

*Color.*—Fully open, upper surface 31A. Fully open, under surface 30D. Half open, upper surface 32A. Half open, under surface 30D.

*Reproductive organs.*—Normal.

I claim:

1. A new and distinct cultivar of Dahlia plant named Simon, as illustrated and described.

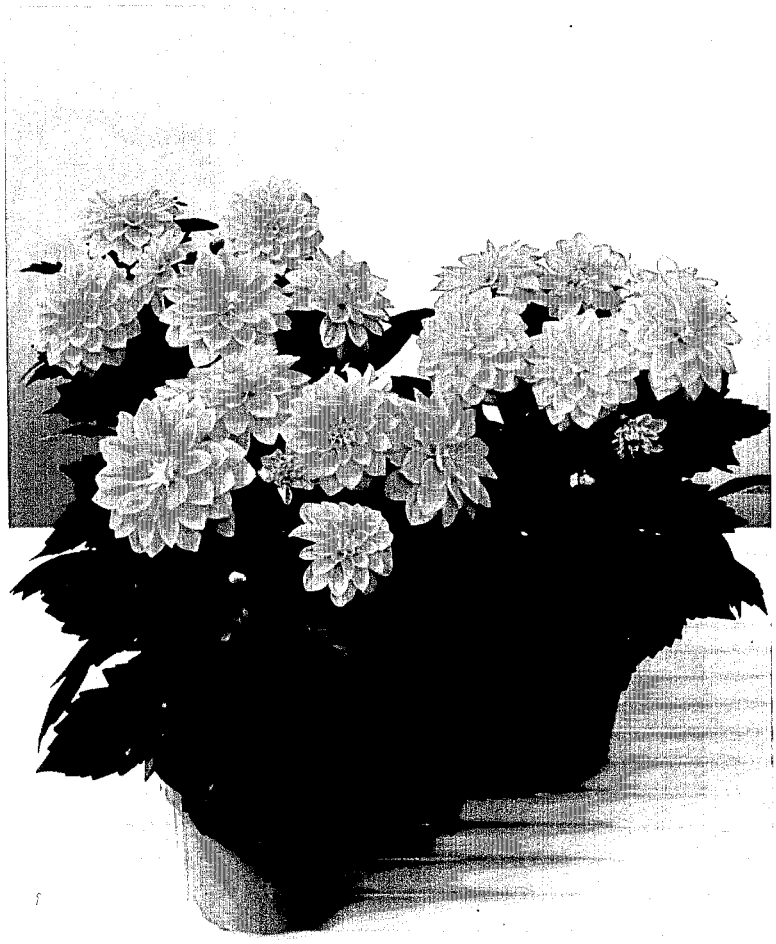

* * * * *